United States Patent [19]

Yamaguchi et al.

[11] Patent Number: 5,001,531
[45] Date of Patent: Mar. 19, 1991

[54] FUNCTIONAL ELEMENTAL DEVICE AND FET SENSOR PROVIDED WITH THE SAME

[75] Inventors: Shuichiro Yamaguchi; Takeshi Shimomura, both of Kanagawa, Japan

[73] Assignee: Terumo Kabushiki Kaisha, Tokyo, Japan

[21] Appl. No.: 520,441

[22] Filed: May 8, 1990

[30] Foreign Application Priority Data

May 10, 1989 [JP] Japan .................................. 1-118347

[51] Int. Cl.⁵ ...................... H01L 29/66; H01L 29/96
[52] U.S. Cl. ......................................... 357/25; 357/61; 357/23.15; 357/65; 204/294
[58] Field of Search ..................... 357/25, 8, 61, 23.15, 357/65, 67; 204/403, 416, 294; 48/DIG. 148; 428/624, 627, 634

[56] References Cited

U.S. PATENT DOCUMENTS 4,137,355  1/1979  Heaps et al. ....................... 357/85 X
4,836,904  6/1989  Armstrong et al. ............. 204/403 X Primary Examiner—Andrew J. James
Assistant Examiner—Sara W. Crane
Attorney, Agent, or Firm—Burns, Doane, Swecker & Mathis

[57] ABSTRACT

A functional elemental device and an FET sensor provided with the same, formed by forming a conductive carbide layer between the substrate and a conductive carbon material layer, and organic thin films and were formed on the surface of said conductive carbon material layer.

Thereby, the adhesiveness between the substrate and the conductive carbon material layer can be remarkably improved, and peeling does not occur in the case of electrolytic polymerization reaction and film formation, and since the interstitial ions and the like from the substrate can be prevented, the lowering of the function can be prevented, and therefore, there is attained such an effect that the preparation of a thin film covered electrode becomes possible.

9 Claims, 3 Drawing Sheets

FUNCTIONAL ELEMENTAL DEVICE AND FET SENSOR PROVIDED WITH THE SAME

BACKGROUND OF THE INVENTION

1. Field of the Invention

The present invention relates to a functional elemental device formed by covering the surface of a conductive carbon material layer with an organic thin film, and an FET sensor using the same.

2. Description of the Prior Art

Conductive carbon material is recently noticed as a material having possibility of wide range development in the sensor, electronic device, electrochromy, electroplating, photochemistry, optical conversion technology, semiconductor technology, and further, in fine processing technology, etc., by being joined with an organic thin film.

By the way, hitherto, the pattern of this conductive carbon material layer has been prepared by adhering conductive carbon such as a carbon paste on a substrate such as the gate of an FET, and by letting the product be subjected to heat solidification or the like.

However, it is extremely difficult to let these conductive carbon materials directly cover on the gate of an FET, and especially, to prepare in a state such that the pattern of the conductive carbon layer is separated from an insulating layer on a fine processing technology pattern (several hundred to several $\mu m$ order), and there was a limit in the size thereof.

Also, even in the case when the conductive carbon material is let directly cover the nitride film ($Si_3N_4$ film) prepared by the dielectrics technology such as the vacuum deposition method, sputtering method, CVD (chemical vapor deposition) method of the recent thin film formation technology, there was the fear that the conductive carbon material layer peels off due to the difference of its thermal expansion coefficient with that of the nitride film. Also, there was such a problem that ions and easily displaceable substances, which are contained in the substrate of the insulating layer or the like such as described above, intrudes into the conductive carbon material layer, and the function as an element lowers.

SUMMARY OF THE INVENTION

The present invention has been carried out in view of such problematic points, and has the object of providing a functional elemental device in which the conductive carbon material layer is strongly adhered with the substrate, and the peeling off due to the difference of thermal expansion coefficient, and further, the lowering of the performance due to the ions and easily displaceable substances contained in respective materials can be prevented, and an FET sensor equipped with the same becomes provided.

In order to solve the above-described problems, the functional element according to the present invention is characterized by being equipped with a substrate, a conductive carbide layer, a conductive carbon material layer formed on said conductive carbide layer and an organic thin film formed on the surface of said conductive carbon material layer.

As the above-described substrate, any of insulating material, semiconductor material, and conductive material may be used, such as, for example, a semiconductor substrate ($SiO_2$ and the like), a silicon substrate, a polysilicon substrate, metal oxide (indium tin oxide (ITO), indium oxide ($InO_2$), iridium oxide ($IrO_2$), palladium oxide (PdO), etc.), an FET gate insulating substrate, nitride film ($Si_3N_4$). quartz, monocrystalline alumina (sapphire) and aluminium oxide.

Also, the carbide layer is the one selected from intrusion type compounds or covalent form compounds. Here, the so-called interstitial compound is the totalized name of one kind of intrusion type solid solutions or crystalline compounds which are formed by the intrusion of atoms of other small non-metal element (for example, hydrogen, boron, carbon, nitrogen, and oxygen) in the gaps of the crystal lattice or atomic lattice of a metal. Examples thereof are shown in Tables 1-1 and 1-2, and Table 2.

Among these compounds, the preferable ones are such compounds that have such characteristics as hard and having high melting point, and moreover, chemically stable, that is, those which do not react with water or acid to produce hydrogen, hydrocarbon, or the like. Also, this intrusion type compound is used especially in the case when the substrate material is a conductive material or a semiconductor material. By the way, as a carbide, it is necessary that the carbide itself has conductive properties.

On the other hand, covalent carbide is formed by bonding (heating) carbon to an oxide, and gives a comparatively hard and chemically stable structural body such as SiC, $B_4C$ ($B_{12}C_3$), etc. In the intermetallic compound of the interstitial compounds, the bond between metal and non-metal is comparatively strong, and there are many ones which owe to the resonance of the covalent bond.

TABLE 1-1

| | | (Interstitial carbides) | | | |
|---|---|---|---|---|---|
| Radius of metal atom | Type of compound | Example | Structure | Characteristics | Production method |
| $\geq 2.4 Å$ (but, V is 1.35Å) | MC | Ti,Zr, Hf,V, Nb,Ta, Mo,W compounds | Carbon atoms enter into gaps of closest packing of metal atoms. In MC, all gaps are filled, in $M_2C$ half is filled. Atom gaps elongates a little. | Opaque, metallic lustre, conductive, hard, high m.p. chemically stable. | Metal + Carbon (heat) |
| | $M_2C$ | V,Ta Mo,W compounds | | | |
| < 1.4Å | $M_3C$ | Mn,Fe, Co, Ni | Due to the intrusion of | Opaque, metallic | |

TABLE 1-1-continued (Interstitial carbides)

| Radius of metal atom | Type of compound | Example | Structure | Characteristics | Production method |
|---|---|---|---|---|---|
| | | compounds | carbon, lattice of metal is considerably strained. | lustre, conductive. React with water or acid to produce $H_2$ and hydrocarbon. | |
| | $M_3C_2$ | Cr compounds | Metal lattice strains considerably, —C—C— continuous chain exists. | | |

TABLE 1-2

(Properties of various kinds of interstitial compounds)

| Compound | Radius ratio | Specific gravity | Melting point (K) | Hardness | Superconductivity temp. (K) |
|---|---|---|---|---|---|
| TiN | 0.49 | 5.18 | 3220 ± 50 | 8–9 | 1.2–1.6 |
| ZrN | 0.45 | 6.93 | 3255 ± 50 | 8+ | 9.45 |
| VN | 0.53 | 5.63 | 2570 | 9–10 | |
| NbN | 0.49 | 8.40 | 2570 | 8+ | |
| TaN | | | 3360 ± 50 | 8+ | |
| TiC | 0.53 | | 3410 ± 90 | 8+ | <1.15 |
| ZrC | 0.48 | | 3805 ± 125 | 8–9 | 2.1–4.1 |
| HfC | | | 4160 ± 150 | | |
| VC | 0.58 | | | 9–10 | |
| NbC | 0.53 | | 3770 ± 125 | 9+ | 10.1 |
| TaC | 0.53 | | 4150 ± 150 | 9+ | 7.6–9.5 |
| MoC | 0.56 | | 2965 ± 150 | 7–8 | |
| $Mo_2C$ | | | 2960 ± 50 | 7–9 | |
| WC | 0.55 | | 3140 ± 50 | 9+ | |
| $W_2C$ | | | 3130 ± 50 | 9–10 | |
| 4TaC.ZrC | | | 4205 | | |
| 4TaC.HfC | | | 4215 | | |
| $TiB_2$ | | 4.0 | | 9+ | |
| $ZrB_2$ | | 5.64 | | | |
| $VB_2$ | | 5.28 | | 8 | |
| $NbB_2$ | | 6.4 | | 9+ | |
| $TaB_2$ | | 11.0 | | 9+ | |
| $WB_2$ | | 10.77 | | 9+ | |
| $ZrB_2$ | | | 3265 ± 50 | 9+ | |
| HfB | | | 3335 | | |
| CrB | | 6.1 | | | |
| WB | | | 3195 ± 50 | | |
| MnB | | 6.12 | | 8 | |
| FeB | | 7.15 | | | |
| CoB | | 7.25 | | about 7–8 | |

TABLE 2

(Intermetallic compound-like classification of various kinds of interstitial compounds)

| Intruding position | Intrusion ratio | Structure | Example |
|---|---|---|---|
| Cubic closest packing | Gaps of octahedron shape | 1 | NaCl type | TiC,TiN,ZrC, ZrN,HfC,UC, NbC,TaC,VC |
| | | ½ | — | $W_2N,Mo_2N$ |
| | | ¼ | — | $Mn_4N,Fe_4N$ |
| | Gaps of tetrahedron shape | 1 | $CaF_2$ type | $TiH_2$ |
| | | ½ | CuCl type | ZrH,TiH |
| | | ¼ | — | $Pd_2H$ |
| | | ⅛ | — | $Zr_4H$ |
| Hexagonal closest packing | Gaps of octahedron shape | ½ | — | $V_2C,Mo_2C$ |
| | Gaps of tetrahedron shape | ½ | — | $Zr_2H,Ti_2H$ |

Also, the one subjected to the super material functional coating by the CVD method has become recently noticed as a high strength engineering functional material in such properties as heat-proofness, high hardness, wear-proofness, high temperature oxidation-proofness anti-corrosion, chemical stability, high (low) thermal conductivity, and electric insulation (conductivity), etc. It is preferable that the coating as described above is applied to the above-described organic thin film. The especially noticed ones are shown in the following Table 3.

Further, as the above-described organic thin film, can be used concretely an ion-sensitive redox functional film, or the one in which an ion selective film has been let to further cover over this film, and further a redox functional film having permeability to a specified gas.

Also, the FET sensor according to the present invention is made by using the gate electrode of an FET or the elongated part thereof or the gate insulating film as the substrate of the above-described functional group, and by uniting a functional element thereto.

TABLE 3

| | | Feature | Use |
|---|---|---|---|
| Ti group | TiC TiN | high melting point, super hard substance | When Tic film is mainly used as a protective film of a cutting tip, its life is lengthened to a large extent. P—TiC film is a protective film of the first inner wall of nuclear fusion furnace. TiN, TiCN film is, other than cutting tip protective film, anti-corrosion protection, utilized as diffusion barrier. Coloring; yellow plane (TiN). |

TABLE 3-continued

| Feature | Use |
|---|---|
| | dark violet (TiCN) |
| SiC Excellent diffusion barrier characteristics | Protective film of graphite susceptor for producing semiconductor element |
| Excellent heat-proof, anti-radiation properties | Anti-environment element, solar cell, thin film thermistor, high heat conductive substrate |
| High temperature antioxidation, corrosion-proof, high temperature strength, heat shock proofness | MHD power generation material, anti-oxydation and anti-wearing coating |
| WC High melting point, Super hard substance | |

In the functional elemental device of the above-described construction and the FET sensor equipped with the same, the conductive carbide layer can approximate the lattice constant, composition and thermal expansion coefficient, respectively, between the grounding substrate and the conductive carbon material layer of the upper layer. As the most preferable method, the method in which the conductive carbide layer is subjected to epitaxial growth on the grounding substrate, and further, the conductive carbon material layer is subjected to epitaxial growth on the conductive carbide layer, is used. Therefore, the conductive carbon material layer does not peel off from the substrate, and the generation of pin holes can be prevented. Also, since the carbide layer intervenes between the substrate and the conductive carbon material layer, there does not occur such a case that the ions and the like in the substrate intrudes into the conductive carbon material layer, and the lowering of the function of the element can be prevented.

As described above in detail, according to the functional element of the present invention and the FET sensor equipped with the same, since a conductive carbide layer was formed between the substrate and the conductive carbon material layer, and an organic thin film was formed on the surface of said conductive carbon material layer, the close adhesiveness between the substrate and the conductive carbon material layer can be remarkably improved, and therefore, no peeling off occurs in the case of the electrolytic polymerization reaction and film formation, and since the intrusion of the ions and the like from the substrate can be prevented, the lowering of the function can be prevented, and therefore, there is attained such an effect that the preparation of the film covered electrode by a thin film becomes possible.

DESCRIPTION OF THE PREFERRED EMBODIMENTS

In the following, embodiments of the present invention will be concretely explained by referring to drawings.

EMBODIMENT 1

Figure 1:
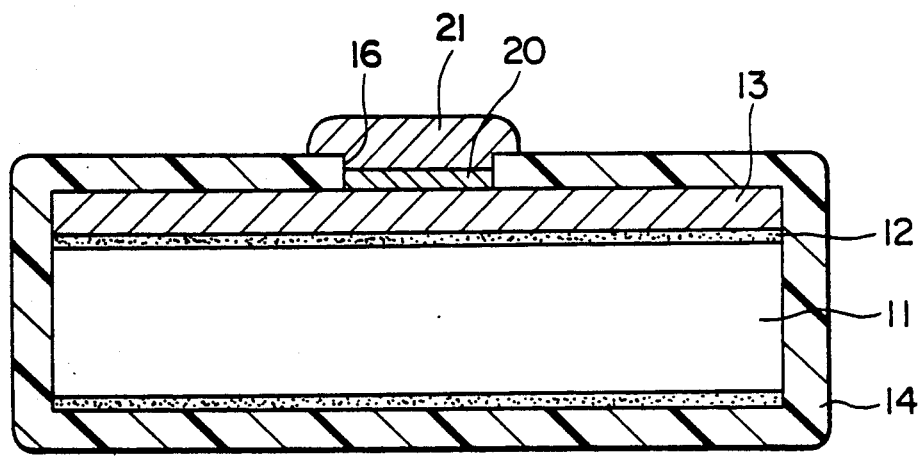
FIG. 1 shows the film covered sensor according to the embodiment 1, and is a sectional diagram along the line 1—1 in FIG. 3.
Figure 2:
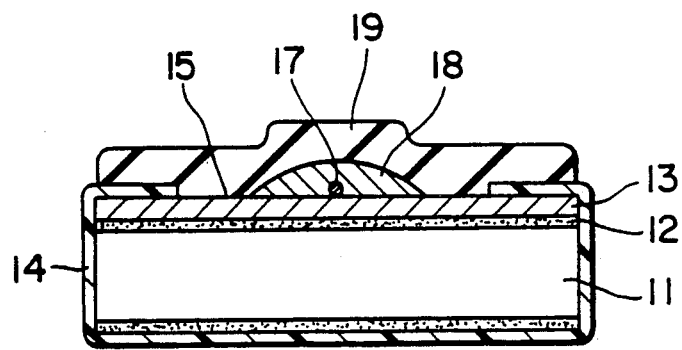
FIG. 2 is a sectional diagram along the line 2—2 in FIG. 3.
Figure 3:
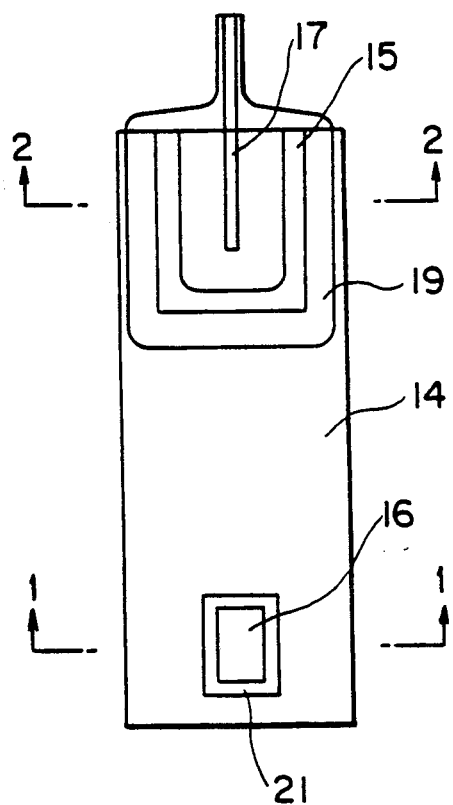
FIG. 3 shows the plane diagram of the film covered sensor of the embodiment 1.

Preparation of Conductive Carbon Material Layer/ SiC Layer/$Si_3N_4$ Layer/Quartz Substrate At first, as shown in FIG. 1 to FIG. 3, an insulating substrate 11 formed with an $Si_3N_4$ (silicon nitride) layer of about 2000 Å on the surface of a quartz substrate by vacuumed thermal CVD method was used, and on the surface of that insulating substrate 11 was formed an SiC (silicon carbide) layer 12 of about 2000 Å by use of the plasma CVD method. Next, by use of the thermal CVD method having methane gas as a raw material, a graphite layer 13 of about 10 μm thickness was formed at the temperature of about 1100° C. The resistance of this graphite layer 13 was measured by use of the four searching needle method, and as a result, it was found that the conductivity is about 100 S cm$^{-1}$ (300 K) and it is possible to utilize it as an electrode material.

Formation of a Redox Functional Film and an Ion Selective Film

The substrate prepared in such a manner as described above was cut in a size of 0.8 mm×5 mm by use of a dicing saw. Next, after covering the pieces by use of a nega type photoresist film 14 and forming the contact part 15 and the electrode part 16 by patterning, the product was electrically connected by adhering a urethane covered copper wire 17 on the contact part 15 by use of a conductive adhesive agent 18, and further, the contact part 15 was electrically insulated by use of a silicone covering film (PRX 305, made by Toray, Ltd.) 19.

Next, by using the electrode prepared as described above as a performance electrode, and by using a saturated sodium chloride calomel electrode (SCE) as a reference electrode and a platinum electrode as a counter electrode, electrolytic oxidation was carried out in a three electrode type cell by using a potentiostat, and a redox functional film 20 was attached and formed on the electrode part 16. That is, as the electrolytic solution at this time, an acetonitrile solution containing 4,4'-biphenol of 0.1 M and $NaClO_4$ of 0.5 M was used, and after effecting sweep electrolysis in the range of 0 to 1.5 V for a SSCE at 20° C. at the speed of 150 mV/sec, electrolysis was effected for 1 minute at 1.5 V to obtain a redox functional film 20 consisting essentially of poly (4,4'-biphenol of about 2 μm thickness.

After washing the substrate prepared in such a manner as described above for several times with pure water and after drying it, the solution for various kinds of ion selective film forming use of about 10 μl of the composition shown in Table 4 was dropped for several times by using a microdispenser, and was dried. This process was repeated for several times, and an ion selective film 21 having the thickness of 10 to 100 μm was formed in such a manner as it covers the whole surface of the redox functional film 20, and various kinds of ion sensors were obtained.

EXPERIMENTAL EXAMPLE 1

Figure 4:
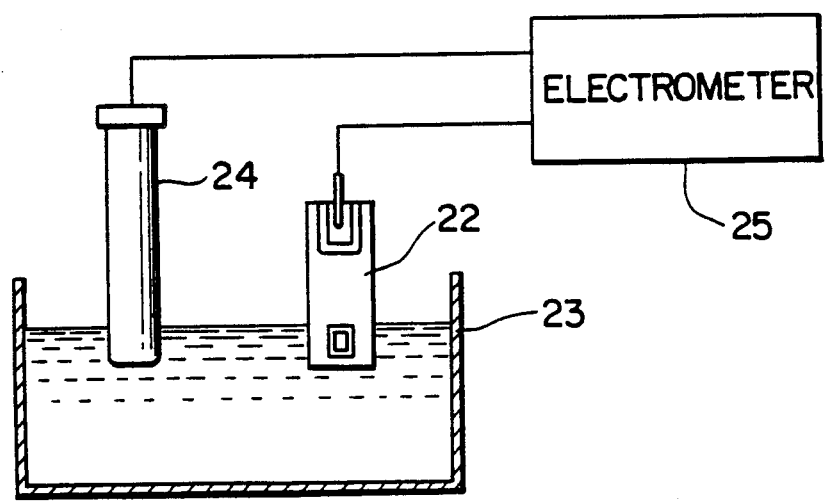
FIG. 4 is a an outline constitutional diagram of the measuring device of the sensor characteristics.

Among the various kinds of ion sensors prepared in the Embodiment 1, the ion sensor for $H^+$ measuring use 22 was immersed in the cell for measurement use 23 shown in FIG. 4 together with the standard electrode 24 of saturated sodium chloride saturated calomel electrode (SSCE), and the electromotive force thereof was measured by use of an electrometer 25 by changing the detected ion concentration.

As a result, it was found that the electromotive force showed good linearity for the pH value in the range of $pH=3$ to 10.0. It was found that the inclination of that straight line was 61 mV/pH (temperature 37° C.) and agrees to the theoretical response characteristics, and that the response time was so rapid as to be less than 4 seconds.

Also, in this electrode, the deterioration due to the peeling off and the like of the graphite layer 3 due to the immersion for long hours was not perceived, and it was known that the adherence between the insulating substrate ($Si_3N_4$) 11 and the graphite layer 13 is improved, and together with that, the intrusion of ions and the like from the substrate could be prevented.

EMBODIMENT 2

Figure 5:
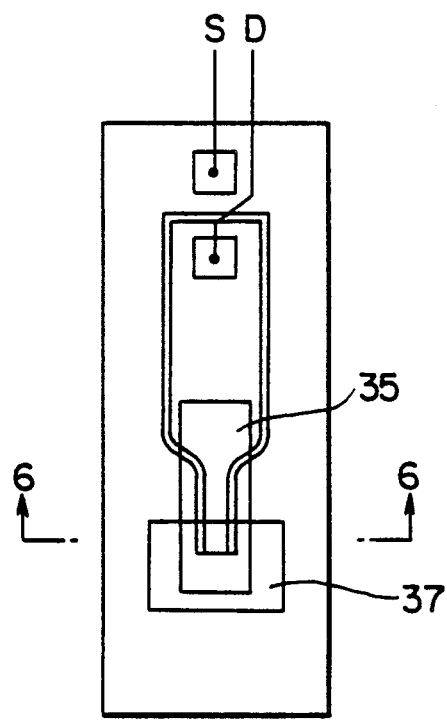
FIG. 5 is a plane diagram of the film covered sensor according to the embodiment 2.
Figure 6:
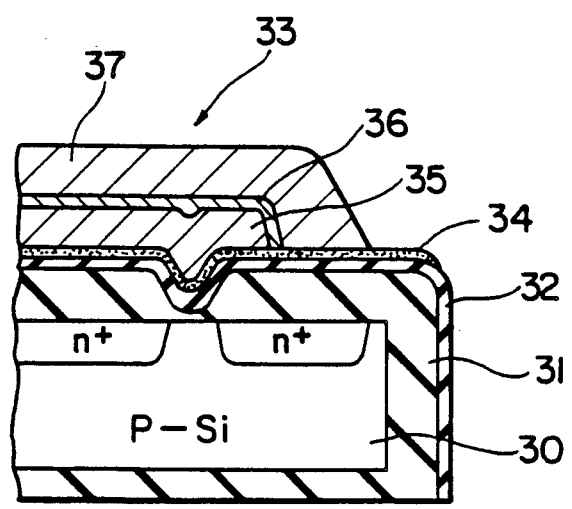
FIG. 6 is a sectional diagram along the line 6—6 in FIG. 5.

Preparation of Conductive Carbon Material Layer SiC Layer/$Si_3N_4$ Layer/ $SiO_2$ Layer Next, the ion sensor shown in FIGS. 5 and 6 was prepared. That is, on the gate part 33 of the MOSFET constituted with an $SiO_2$ film 31 of film thickness of 1000 Å and $Si_3N_4$ film 32 of film thickness of 1500 Å formed on the surface of a P-type silicon substrate 30 was carried out by sputtering for 3 to 10 minutes under the conditions of 13.56 MHz and 800 W by use of an RF sputtering device, and an SiC layer 34 of the thickness of about 800 Å was formed. At this time, in order to form SiC layer 34 on the gate part only, a metal mask was used. Next, after exchanging the target with graphite in the same sputtering device, sputtering was carried out to form graphite layer 35 of the thickness of about 2 μm.

Formation of Redox Functional Film and the Ion Selective Film

At a terminal of the graphite layer 35 formed in such a manner as described above, was press contacted a contact needle to form an acting electrode, and in similar manner as in the Embodiment 1, a redox functional film 36 consisting essentially of poly (4,4'-biphenol) of about 2 μm thickness was formed on the surface of the graphite layer 35. Then, furthermore, the solutions for various kinds of ion selective film forming use of the composition shown in Table 4 was dropped on the surface of the redox functional film 36, and by repeating the coating and drying, an ion selective film 37 of the film thickness of 10 to 100 μm was formed, and various kinds of ion sensors were obtained. However, before forming this ion selective film 37, the contact part of the graphite layer 35 was electrically insulated by use of a silicone adhesive agent.

TABLE 4

| Experimental example | Ions to be detected | Ion carrier composition | | KTpClPB mg/ml | PVC mg/ml | DOS mg/ml |
|---|---|---|---|---|---|---|
| | | Carrier substance and content mg/ml | | | | |
| 1, 9 | $H^+$ | TDDA | 8 | 1.2 | 65.0 | 130.0 |
| 2, 10 | $Na^+$ | Bis-12-Crown-4 | 8 | 1.2 | 65.0 | 129.0 |
| 3, 11 | $K^+$ | Varinomycine | 3.2 | — | 65.6 | 131.2 |
| 4, 12 | $NH_4^+$ | Nonactine | 6.2 | 1.2 | 80.8 | 161.8 |
| 5, 13 | $Cl^-$ | TPSnCl | 11.2 | — | 63.0 | 125.8 |
| 6, 14 | $Ca^{2+}$ | $Ca(DOPO)_2$ | 14.0 | | | |
| | | DOPO | 62.0 | — | 62.0 | 62.0 |
| 7, 15 | $Mg^{2+}$ | DHDMBA | 6.2 | 1.2 | 80.5 | 160.0 |
| 8, 16 | $Li^+$ | | | | | |

EXPERIMENTAL EXAMPLES 2 to 8

Among the various kinds of ion sensors prepared in the Embodiment 1, the sensor for ion use other than $H^+$ was used, and similarly examined $Na^+$ (experimental example 2), $K^+$ (experimental example 3), $NH_4^+$ (experimental example 4), $Cl^-$ (experimental example 5), $Ca^{2+}$ (experimental example 6), $Mg^{2+}$ (experimental example 7), and $Li^+$ (experimental example 8), but in any of them, good characteristics (sensitivity; mV/pH, draft stability, etc.) were obtained.

Solvent: THF (tetrahydrofurane)
TDDA: tridodecyl amine
Bis-12-Crown-4: Bis [(12-crown-4) methyl]dodecyl malonate (made by Dojin Chemical Laboratory)
Varinomycine: (made by Sigma Co.)
Nonactine: (containing 25% nonactine, made by Sigma Co.)
TPSnCl: triphenyl tin chloride (made by Aldrich Co.)
$Ca(DOPO)_2$: calcium bis [di-(n-octylphenyl)phosphate] (made by Dojin Chemical Laboratory)
PVC: polyvinyl chloride
DOS: sebacic acid di(2-ethylhexyl)

EXPERIMENTAL EXAMPLES 9 to 16

By the use of the various kinds of ion sensors prepared in the Embodiment 2, the following ions were examined by taking them as the ions to be detected: $H^+$ (experimental example 9), $Na^+$ (experimental example 10), $K^+$ (experimental example 11), $NH_4^+$ (experimental example 12), $Cl^-$ (experimental example 13), $Ca^{2+}$ (experimental example 14), $Mg^{2+}$ experimental example 15), and $Li^+$ (experimental example 16). In any of them, good sensor characteristics (sensitivity, drift stability, etc.) were obtained.

EMBODIMENT 3

Preparation of Conductive Carbon Material Layer/ SiC Layer/Polysilicon Layer/$Si_2N_4$ Layer/$SiO_2$ Layer After forming a polysilicon layer of the thickness of about 500 Å at the gate part of MOSFET of $SiO_2$-/$Si_3N_4$ structure by use of a reduced pressure CVD device, $CH_4$ (methane) was heat decomposed by use of the same CVD device to form a graphite layer of the thickness of about 2 μm. Next, at the temperature of 1150° C. annealing (heat treatment) was effected for 5 hours in an inert gas stream to form a β-SiC layer in the interface of the polysilicon layer and the graphite layer. Next, in similar manner as in the Embodiments 1 and 2, an ion selective film was formed.

Formation of Redox Functional Film

In similar manner as in Embodiment 1, after connecting an urethane covered copper wire by use of a conductive adhesive agent to the end terminal part by cutting the graphite covered substrate prepared as described above in a size of 0.8 mm×5 mm, the product was electrically insulated by use of a silicone covering agent (PRX 305) except the end terminal part (0.8 mm×0.8 mm).

Next, by using the electrode prepared in such a manner as described above as a performance electrode, in similar manner as in the Embodiment 1, an oxidation reduction functional film consisting of meso-tetra(o-aminophenyl) porphiline cobalt was formed on the electrode surface under the electrolytic conditions as described in the following.

Composition of the Electrolytic Solution

Meso-tetra(o-aminophenyl) porphiline cobalt: 1 m mol/l 0.1 mol/l
Sodium perchlorate: 0.1 mol/l
Solvent: Acetonitryl

Electrolytic Conditions

After effecting potential sweeping for three times at room temperature and in a nitrogen gas stream at the speed of 50 mV/sec from 0 V to 1.8 V (versus SSCE), the product was subjected to constant potential electrolysis at 1.8 V for 3 minutes.

EXPERIMENTAL EXAMPLE 17

The oxygen sensor prepared in the Embodiment 3 was immersed in a cell for oxygen partial pressure measuring use, and was subjected to constant potential electrolysis at −0.6 V (versus SSCE) by changing the oxygen partial pressure. As a result of measuring the current value at this time, good linear relationship was shown at the oxygen partial pressure of 10 to 600 mmHg. Therefore, it was known that the measurement of the oxygen partial pressure concentration can be carried out on a conductive carbon material gate using a silicone substrate by the polymeso-tetra(o-aminophenyl) porphyline cobalt film.

EXPERIMENTAL EXAMPLE 18

By covering the surface of the oxygen electrode prepared in the Embodiment 3 with the enzyme fixed film bridge-formed with glucose oxidase together with albumin by use of glutamine aldehyde, a glucose sensor was prepared. By use of this electrode, glucose concentration was measured, and characteristics of the sensitivity of 45 mV/log concentration and the response time of less than 5 minutes was obtained in the concentration range of 1~300 mg/dl.

By the way, although in the above-described Embodiments, examples in which the present invention was applied on an ion sensor, a gas sensor and an enzyme sensor were explained, but it can of course be utilized in other cases such as the flow electrode, voltammetry electrode, etc.

What is claimed is:

1. A functional elemental device comprising:
   a substrate;
   a conductive carbide layer formed on the surface of said substrate;
   a conductive carbon material layer formed on said conductive carbide layer; and
   an organic thin film formed on the surface of said conductive carbon material layer.

2. The functional elemental device according to claim 1, wherein said carbide layer is an interstitial compound.

3. The functional elemental device according to claim 1, wherein said carbide layer is a covalent compound.

4. The functional elemental device according to claim 1, wherein said organic thin film is a protective film which maintains the characteristics of the conductive carbon material, and has protective action for environment.

5. The functional elemental device according to claim 1, wherein said organic thin film is an ion-sensitive redox functional film.

6. The functional elemental device according to claim 5, wherein said external surface of the redox functional film is further covered with an ion selective film.

7. The functional elemental device according to claim 1, wherein said organic thin film is a redox functional film having gas permeable properties for sensing a specified gas.

8. An FET sensor comprising:
   a field effect transistor;
   a conductive carbide layer formed on the gate electrode of said field effect transistor or on the surface of the elongated part thereof;
   a conductive carbon material layer formed on said conductive carbide layer; and
   an organic thin film formed on the surface of said conductive carbon material layer.

9. An FET sensor comprising:
   a field effect transistor;
   a conductive carbide layer formed on the surface of the gate insulating film of said field effect transistor;
   a conductive carbon material layer formed on said conductive carbide layer; and
   an organic thin film formed on the surface of said conductive carbon material layer.

* * * * *